United States Patent [19]
Schembri

[11] Patent Number: 5,693,233
[45] Date of Patent: Dec. 2, 1997

[54] METHODS OF TRANSPORTING FLUIDS WITHIN AN ANALYTICAL ROTOR

[75] Inventor: Carol T. Schembri, San Mateo, Calif.

[73] Assignee: Abaxis, Sunnyvale, Calif.

[21] Appl. No.: 566,982

[22] Filed: Dec. 4, 1995

Related U.S. Application Data

[62] Division of Ser. No. 124,525, Sep. 20, 1993, Pat. No. 5,472,603, which is a continuation of Ser. No. 862,041, Apr. 2, 1992, abandoned.

[51] Int. Cl.$^6$ .................. B01D 21/26; B04B 11/00; B04B 11/06
[52] U.S. Cl. .................. 210/787; 210/377; 210/380.1; 210/782; 422/72; 436/45
[58] Field of Search .................. 210/782, 787, 210/360.1, 380.1, 377, 378, 512.1; 422/72, 100, 102, 104; 436/45; 356/246; 494/16, 17, 37

[56] References Cited

U.S. PATENT DOCUMENTS

| | | | |
|---|---|---|---|
| 3,795,451 | 3/1974 | Mailen | 356/246 |
| 3,829,223 | 8/1974 | Hamel | 356/246 |
| 3,864,089 | 2/1975 | Tiffany et al. | |
| 3,873,217 | 3/1975 | Anderson et al. | 356/246 |
| 3,881,827 | 5/1975 | Gilford et al. | 356/246 |
| 3,899,296 | 8/1975 | Mailen et al. | 422/72 |
| 4,225,558 | 9/1980 | Peterson et al. | 422/72 |
| 4,279,862 | 7/1981 | Bretaudiere et al. | 422/72 |
| 4,284,602 | 8/1981 | Kelton et al. | 422/72 |
| 4,387,164 | 6/1983 | Hevey et al. | 436/45 |
| 4,469,793 | 9/1984 | Guigan | 422/72 |
| 4,509,856 | 4/1985 | Lee | 356/246 |
| 4,515,889 | 5/1985 | Klose et al. | 422/72 |
| 4,689,203 | 8/1987 | Kaartinen et al. | 422/72 |
| 4,695,164 | 9/1987 | Zivitz et al. | 356/247 |
| 4,847,205 | 7/1989 | Burtis et al. | 422/72 |
| 4,894,204 | 1/1990 | Cornut | 422/72 |
| 4,898,832 | 2/1990 | Klose et al. | 422/72 |
| 5,061,381 | 10/1991 | Burd | 422/72 |
| 5,122,284 | 6/1992 | Braynin et al. | 210/782 |
| 5,160,702 | 11/1992 | Kopf-Sill et al. | 422/72 |
| 5,173,193 | 12/1992 | Schembri | 210/380.1 |
| 5,186,844 | 2/1993 | Burd et al. | 210/782 |
| 5,242,606 | 9/1993 | Braynin et al. | 210/787 |
| 5,256,376 | 10/1993 | Callahan et al. | 422/72 |
| 5,304,348 | 4/1994 | Burd et al. | 422/72 |

*Primary Examiner*—John Kim
*Attorney, Agent, or Firm*—Townsend and Townsend and Crew LLP

[57] ABSTRACT

The present invention provides an analytical rotor which holds a fluid in a chamber, typically to allow mixing with a reagent, and transfers the fluid to a receiving chamber in the rotor. The rotor comprises a holding chamber having an single exit duct and a receiving chamber connected to the holding chamber through the exit duct. The exit duct prevents flow at a first rotational speed and allows flow at a second, higher rotational speed. The exit duct may include a capillary passage in which capillary forces prevent flow until the rotational speed is increased. Alternatively, the exit duct may include a siphon.

10 Claims, 1 Drawing Sheet

METHODS OF TRANSPORTING FLUIDS WITHIN AN ANALYTICAL ROTOR

This is a division of application Ser. No. 08/124,525 filed Sep. 20, 1993, U.S. Pat. No. 5,472,603, which was a continuation of Ser. No. 07/862,041, filed Apr. 2, 1992, now abandoned.

The present invention is related to the inventions disclosed in the following copending applications: Ser. No. 07/532,524, now U.S. Pat. No. 5,061,381 Ser. No. 07/678,824, now U.S. Pat. No. 5,122,284 Ser. No. 07/678,762 now U.S. Pat. No. 5,186,844 Ser. No. 07/678,823, now U.S. Pat. No. 5,173,193 and Ser. No. 07/747,179, now U.S. Pat. No. 5,413,732 the disclosures of which are incorporated herein by reference.

BACKGROUND OF THE INVENTION

1. Field of the Invention

The present invention relates generally to devices and methods for analyzing biological fluids. In particular, it relates to the design and use of centrifugal rotors which allow mixing a fluid with a reagent and delivery of that mixture to a chamber in the rotor.

Tests on blood plasma and other biological tests frequently require quick mixing of samples and reagents, and quick delivery of the resulting mixture from one portion of the rotor to another for analysis. The analysis may be a variety of optical, biological, or chemical tests or assays.

It is frequently desirable to separate cellular components from the liquid fraction of biological material prior to testing because the cellular component can interfere with certain analyses. Typically, centrifugation separates the biological material into cellular and fluid fractions. For instance, centrifugation separates whole blood into cells and plasma.

Subsequently, predetermined volumes of plasma are transferred to separate test wells by manual or automated methods. Additionally, various reagents are generally required. Usually precise quantities of these reagents must be mixed with plasma or other biological fluids. Because these procedures are labor intensive and time-consuming, assorted automated systems and methods have been proposed to more efficiently provide reagent mixing and fluid transfer to various vessels suitable for testing.

Of particular interest to the present invention are centrifugal rotors which have been modified to mix a biological fluid with an appropriate reagent or diluent. These rotors may additionally include modifications for separation of fluid from cellular components. Furthermore, appropriate alterations may permit transfer of fluid from one vessel to another. Finally, such rotors may provide a plurality of discrete test wells to facilitate testing or evaluation.

Prior art rotors have frequently utilized complex designs which are costly and difficult to manufacture. Often, the rotors require various separable parts which are brought together or separated at different points in the centrifugation procedure. Previous centrifugal rotors have often been limited in the number of discrete samples and test wells which they can provide. In some cases, these rotors require use of a separate displacement fluid to effect flow of blood and plasma through the system.

For these reasons, it would be desirable to provide improved centrifugal rotors and methods suitable for quickly and easily mixing a volume of fluid with a reagent, and for transferring the resulting mixture from its mixing vessel to another chamber. The fluid could be transferred, for example, into chambers suitable for separation of cellular components and ultimately distributed into test wells for analysis within the rotor. Additionally, the rotors should be capable of mixing and distributing relatively small volumes of fluid.

The rotors should be able to accommodate relatively large numbers of test wells or cuvettes, and the rotor design should be simple and amenable to low-cost manufacture. It would be particularly desirable if the rotors were of unitary construction with no separable or movable parts. Liquid mixing methods should be simple and performable in relatively short times. The methods should require relatively few steps and minimal human intervention. It would be advantageous if the methods required only rotation of the rotor in order to effect mixing and delivery of the fluid.

2. Description of the Background Art

U.S. Pat. No. 4,894,204 to Cornut discloses a centrifugal rotor having a calibration vessel connected to an overflow vessel. The calibration vessel has a feed orifice through which it communicates with a central receptacle and an exit orifice located in the wall opposite the feed orifice. The exit orifice is designed such that liquid begins to escape from the calibration vessel from the start of its being filled.

U.S. Pat. No. 4,898,832 to Klose describes a rotor which includes dried reagents adsorbed or bound to a solid carrier. A sample solution is moved along the rotor by use of centrifugal force and/or pressure force.

U.S. Pat. No. 3,829,223 to Hamel discloses a rotor adapted for mixing sample and reagent for photometric analysis in the rotor. Ramp-like projections on the walls of the test wells assist with mixing.

U.S. Pat. No. 3,795,451 to Mailen teaches a rotor for mixing a sample and reagent using a variation in rotational speed to provide mixing. A capillary passage is fed at increased rotational speeds to transfer the liquid as flow over a steep angle is permitted.

U.S. Pat. No. 3,873,217 to Anderson describes a rotor for photometric analysis using static loading of a main cavity and distribution of liquid to cuvettes using dynamic loading caused by rotational forces.

U.S. Pat. No. 4,387,164 to Hevey relates to chemical analyses of assay mediums and describes using reagents dispersed in soluble film.

U.S. Pat. No. 3,881,827 to Gilford teaches an apparatus and chamber for measuring cardiac output and includes a chamber for mixing a precise amount of dye with blood.

U.S. Pat. No. 4,225,558 to Peterson discloses a fluid test apparatus for multiple fluid samples. A sample and reagent are held in separate chambers until centrifugal force provides migration of the two fluids to a common chamber.

U.S. Pat. No. 3,864,089 describes a rotor for blood fractionation. U.S. Pat. No. 4,279,862 to Bretardiere is directed to a rotor which has means for creating a pressure differential and/or turbulence to produce a homogeneous mixture of reagent and sample. U.S. Pat. No. 4,509,856 is directed to a rotor useful for photometric analysis of a sample. U.S. Pat. No. 4,515,889 relates to the rotor having a plurality of interconnected small hollow spaces adapted for mixing reaction components. U.S. Pat. No. 4,689,203 relates to a centrifugal rotor designed for separating blood plasma from red and white blood cells.

The following U.S. patents relate to rotors providing measurement of a predetermined volume as the rotor spins. U.S. Pat. No. 3,899,296 to Mailen describes a rotor for whole blood samples in which the cellular component is separated from the plasma and measured subvolumes of the plasma are distributed to sample analysis cuvettes. Delivery of the measured volumes is obtained by applying a slight positive air pressure to the passageways containing the plasma. U.S. Pat. No. 4,469,793 relates to centrifugal rotor having a measurement chamber having inlet and outlet orifices. The outlet orifice leads to passages which carry liquid to an overflow chamber when the rotor is rotating in a first direction and to a receptor cell when the rotor is rotating in a second, opposite direction. U.S. Pat. No. 4,284,602 describes a rotor which uses a heavy displacement fluid to transfer a measured amount of sample fluid.

SUMMARY OF THE INVENTION

The present invention provides analytical rotors adapted to hold fluid in a chamber and to deliver fluid to another chamber also in the rotor. Also provided are methods for use of the rotors. The fluid is held in a chamber to allow various manipulations of the fluid. Typically the manipulation involves mixing the fluid with another substance, such as a diluent or a dye. The rotor comprises a holding chamber, adapted to contain a fluid, and a receiving chamber connected to the holding chamber.

The holding chamber is provided with one or more exit ducts which connect the holding chamber to the receiving chamber. Typically, the exit ducts are positioned on the radially outward wall of the holding chamber such that fluid enters the receiving chamber as the rotor is spun. The exit ducts and passages from the holding chamber to the receiving chamber restrict flow of fluid to the receiving chamber so that movement of fluid to the receiving chamber can be controlled. A fluid, such as blood, or a reagent, such as a diluent, or both a fluid and a reagent, may be placed in the holding chamber.

In one embodiment, the exit duct connecting the receiving chamber to the holding chamber includes a capillary passage having a cross sectional area which prevents flow of fluid into the receiving chamber at a first rotational speed and allows flow at a higher rotational speed. The fluid can be held in the holding chamber for as long as desired before delivery to the receiving chamber. At the second, higher rotational speed, centrifugal force exceeds the capillary force and the contents of the holding chamber are transferred to the receiving chamber.

In another embodiment, the connecting means can be a siphon having an elbow that is substantially the same distance from the center of the rotor as the radially most inward point of the holding chamber. As the rotor is spinning the fluid does not flow past the elbow. After the rotor stops or slows sufficiently, capillary forces "prime" the siphon by pulling fluid just around the elbow. When the rotor is restarted, the combination of centrifugal and capillary forces draws the remaining fluid out of the holding chamber into the receiving chamber.

The receiving chamber is typically a separation chamber having a cell trap for separating cellular material from blood plasma. The separated plasma is usually distributed to a collection chamber. The collection chamber may be connected to a plurality of cuvettes in which the biological fluid is analyzed.

The rotor of the present invention is preferably made of clear plastic, more preferably acrylic. Each cuvette typically contains reagents necessary for a biochemical analysis of the fluid in the cuvette.

In addition to the above features, the invention provides methods for mixing and delivering fluid in an analytical rotor. These methods are discussed in detail below.

Upon consideration of the detailed description of the preferred embodiments and the attached drawings set forth below, other advantages of the subject invention will be apparent to those skilled in the art.

DETAILED DESCRIPTION

Figure 1:
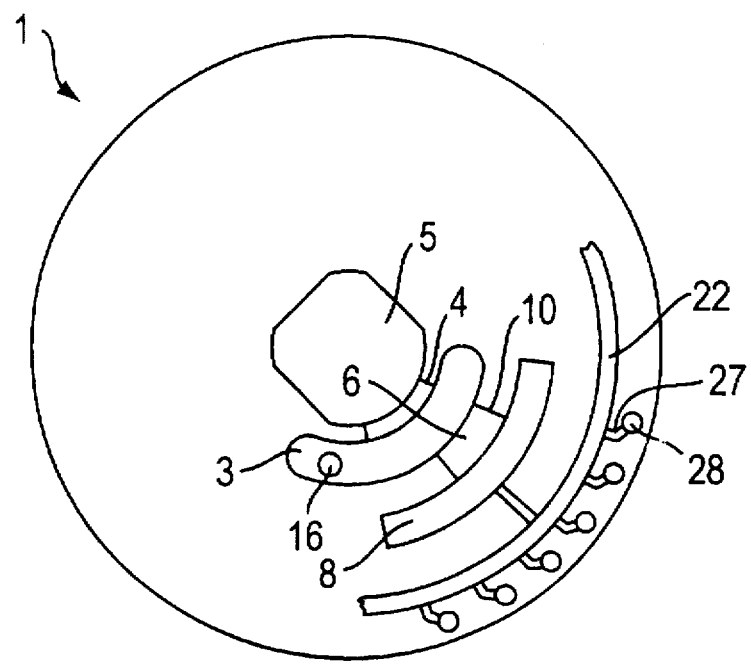
FIG. 1 is a plan view of a rotor designed in accordance with one embodiment of the present invention in which a holding chamber includes a reagent-coated bead; the holding chamber and a receiving chamber are connected by an exit duct which is connected to a capillary passage.

The present invention provides devices and methods for retaining fluid in a holding chamber and transferring the fluid to a receiving chamber. These steps take place in a centrifugal rotor. Usually the fluid is retained in the holding chamber to perform some manipulation on the fluid.

A number of manipulations can be conveniently performed in the holding chamber. For example, the fluid can be mixed with a reagent such as a diluent or a dye. The reagent may be in liquid form or be attached to the chamber wall or attached to a solid matrix or surface placed in the chamber. For example, the reagent may be placed within the chamber as a reagent bead, pellet or other form.

In addition various chemical reactions can be performed. Examples of reactions to occur in such a chamber are heterogeneous immunochemistry reactions or any chemical reaction which takes place in discrete steps.

Other embodiments include measurement of the fluid's optical density in the holding chamber prior to moving the fluid to cuvettes for further optical measurements. This approach would allow one to make comparisons or detect changes. Another application is to allow a precipitate to form, settle and then decant the supernatant. Further, optical techniques to measure the volume or height of the fluid or precipitate could be employed.

Alternatively, the fluid may be held in the holding chamber until some function is completed elsewhere in the rotor. For instance, the fluid may be held until a second fluid has been introduced into the chamber for mixing or reaction. This function can be used with the siphon embodiment. Capillarity of the mouth of the siphon is not provided so that the fluid will not enter the siphon by capillary force when the rotor is stopped. However, when the second fluid enters the chamber, the fluid level in the chamber increases and the siphon moves radially inward. This moves the fluid into the region of the siphon which has surface properties which allow for capillarity. When the rotor stops, the siphon primes as described below.

The holding chamber has a means for introducing fluid therein. Introduction of fluid could be accomplished by any number of means known to the artisan. The fluid could be pipetted, injected through a membrane, or poured. For example, a top layer of the rotor typically includes a blood application port which penetrates the entire thickness of the top layer and is aligned with the holding chamber. This blood application port may conveniently be formed in the top layer by machining, e.g., drilling.

The holding chamber may contain a diluent, or other reagent, which is preloaded in the rotor for storage until the rotor is used. For example, a reagent, such as a dye, may be coated onto a solid surface within the holding chamber. A bead within the holding chamber provides a convenient solid surface for this purpose. If the reagent is a diluent, it is preloaded in the rotor in a container which is not the holding chamber. Means are provided to move the diluent from the diluent container in the holding chamber. Then the diluent is mixed with the dye or reagent as necessary.

The reagents of the present invention may also comprise marker compounds which allow the user to quickly and easily determine dilution in situ. The marker compounds of the present invention are typically photometrically detectable compounds which are added in predetermined or measurable amounts to the diluent. After mixing the diluent with the sample, the concentration of the marker is photometrically determined. This can be done, for instance, by comparing the absorbance of the diluted sample at the appropriate wavelength to standard solutions of known concentration. The ratio of the concentrations of the marker before and after mixing can then be used to determine the amount of dilution of the sample.

Various photometrically detectable marker compounds can be used, including compounds which yield a color reaction. Ideally, the marker compound does not absorb at the wavelengths used in the analyses or cause interference with subsequent assays performed on the sample. Dyes such as 1,1',3,3,3',3'-hexamethylindotricarbocyanine iodide or 1,1'-bis(sulfoalkyl)-3,3,3',3'-tetramethylindotricarbocyanine salts are typically used.

Suitable marker compounds which are converted to photometrically detectable compounds include enzyme substrates not normally present in the sample, such as p-nitrophenyl phosphate or D-lactate. The compound p-nitrophenylphosphate is a substrate for alkaline phosphatase and yields a colored p-nitrophenol reaction product. D-lactate is a substrate for D-lactate dehydrogenase and when used with AND produces the colored NADH reaction product.

Other suitable markers may include enzymes which, upon reaction with substrates, produce color. The enzymes should not normally be present in the sample. The substrates may either be present in the plasma or in the reaction chambers. For samples of human origin, typical enzymes include microbial glucose-6-phosphate dehydrogenase and D-lactate dehydrogenase.

Obviously, the marker compound is preferably selected to minimize interference with any subsequent assays performed on the sample. In cases where the marker compound is unstable and long term storage of the diluent is not practical, the marker or its precursor can be held in the dry state and solubilized near or at the time of its use. For example, 1,1'-bis(sulfoalkyl)-3,3,3',3'-tetramethylindotricarbocyanine salts aggregate after solubilization in aqueous solutions. To prevent this problem, the indocyanine dyes and other unstable dyes are typically stored in a dry form applied to a solid surface in the holding chamber.

The solid surface may be the wall of a passage or chamber in the analytical rotor. Alternatively, the surface may be an inert carrier, such as a polystyrene ball. A suitable isotonic diluent solution may dissolve the dye off the surface at an appropriate time. The aqueous diluent is selected according to the particular dye used. For indocyanine dyes, 2.5% myo-inositol is suitable.

The fluid and the reagent are mixed, typically by rotation of the rotor at a first rotational speed. Rotation may be carried out in only one direction, or it may alternate directions to accomplish mixing. After satisfactory mixing, the fluid is delivered to the receiving chamber through the exclusive exit duct of the holding chamber.

The exit duct may control flow out of the holding chamber so that fluid is delivered to the receiving chamber only after some predetermined time or event. Typically, delivery is delayed until after the holding chamber contains an appropriate volume of sufficiently mixed fluid. The exit duct is designed such that essentially no detectable fluid escapes prematurely from the holding chamber. No detectable fluid is considered to have escaped from the holding chamber if the total volume of fluid ultimately delivered to the receiving chamber is sufficiently accurate that subsequent analyses are not adversely affected.

The control of flow from the holding chamber to the receiving chamber is preferably accomplished by use of a capillary passage. For instance, the exit duct may be of capillary dimensions and connect to a capillary passage in which capillary forces prevent flow at a first rotational speed. When the speed is increased to a second, higher rotational speed, centrifugal force exceeds the capillary force and the holding chamber is emptied.

The capillary passage need not include the entire flow path from the exit duct to the receiving chamber. In some cases it may be preferable that only a portion of the path possess capillary dimensions so long as flow is appropriately controlled. For example, a particular application of the present invention may require an exit duct dimensioned substantially larger than capillary size, followed by an equivalently sized channel for some distance before the capillary passage is encountered. The precise length and cross sectional shape of the capillary passage are not critical to the inventive concept. That the capillary passage is dimensioned to prevent flow at a first rotational speed is essential.

Another preferred embodiment provides an exit duct which connects to a siphon to control flow. Generally a siphon possesses an elbow which is at substantially the same distance from the center of the rotor as the minimum radial point (i.e., the radially most inward point) of the holding chamber. After the holding chamber is filled and the rotor is stopped or sufficiently slowed, capillary action pulls the fluid just beyond the elbow. A siphon in which the fluid has moved to this point as a result of capillary action is considered to be "primed." After the rotor is restarted or its speed increased, the combination of centrifugal force and fluid entrainment pulls the fluid out of the holding chamber and into the receiving chamber.

If the fluid is one which contains cellular or nonliquid material, such as whole blood, the receiving chamber is usually a separation chamber designed to separate fluid (e.g., plasma) from cellular material. The separation chamber typically includes a cell trap. Another example of a receiving chamber is a metering chamber to partition or split a fluid between chambers. For example, fluid would be directed from a holding chamber to a metering or splitting chamber sized to accept a predetermined amount of fluid. Any excess fluid would flow from the splitting chamber to an overflow chamber. This flow partition or metering function is discussed more fully in co-pending application Ser. No. 07/678,823.

The receiving chamber is typically fluidly connected to a collection chamber. The collection chamber may terminate in a plurality of smaller chambers or cuvettes. Further tests may be performed on the fluid in the cuvettes. Thus the rotor also provides for distribution of the diluted or treated fluid into a plurality of test wells or cuvettes. These cuvettes may contain additional reagents. This process allows performance of different analytic procedures without having to transfer aliquots of fluid, such as plasma, from the apparatus.

A multitude of reagents known to those skilled in the art are suitable for use in the present invention. The reagent may be a diluent. For instance, standard diluents such as normal saline solution (0.9% NaCl in water), phosphate buffered solution, Ringer's lactate solution and the like may be used. The reagent may include a marking compound. For example, a dye, a radioactive label, a fluorescent substance, or an immunological compound such as an antigen or antibody may be employed. The above steps for mixing and transferring the treated fluid preferably occur as a result of centrifugal force generated by the spinning rotor.

The apparatus is easy to manufacture and can be produced at low cost. As a result, the apparatus may be offered as a single use disposable unit. Such a feature is particularly desirable in testing whole blood samples which may carry infectious disease. The apparatus can provide for automatic combination of a biological fluid with a predetermined amount of reagent or diluent. Additionally, the apparatus can apportion substantially equal volumes of plasma among the plurality of cuvettes. More importantly, the apparatus is suitable for use with a variety of conventional analytic measurement devices, such as spectrophotometers and fluorometers, which allow individual examination of plasma in the cuvettes within the rotor. This obviates removal of plasma from the rotor before analysis.

Although the present invention is particularly suitable for analyzing diluted or undiluted plasma, it will be useful with a wide variety of other fluids, especially biological fluids. Examples include urine, sputum, semen, saliva, ocular lens fluid, cerebral fluid, spinal fluid, gastric fluid, amniotic fluid, and tissue culture media, as well as food and industrial chemicals, and the like.

Where it may be desirable to separate cells or interfering substances prior to analysis or assay, the devices and methods described in copending application, U.S. Ser. No. 07/532,524 (which is incorporated herein by reference) are preferably used. That application discloses a centrifugal rotor for separating plasma from whole blood. The rotor includes a plurality of internal chambers and passages for combining the plasma with one or more reagents and distributing the mixture to a plurality of individual test wells. The chambers and passages necessary for separating whole blood into plasma are located radially outward from the holding chamber. The separation chamber includes a radially-outward cell trap and a radially-inward drainage port so that spinning of the rotor causes the cellular components of the whole blood to enter the cell trap, while cessation of spinning allows the separated plasma to flow downward through the drainage port. A collection chamber is formed at a level lower than the rotor to receive the plasma through a drainage port.

In the present invention, the collection chamber can formed as noted in the invention of application Ser. No. 532,524 above. Alternatively, the collection chamber can be located on the same level as the separation chamber and separated plasma can flow to the collection chamber by means of centrifugal, rather than gravitational, force.

The distribution of fluid to cuvettes or test wells is preferably accomplished using the general methods and devices disclosed in copending application U.S. Ser. No. 07/678,824, which is incorporated herein by reference. That application discloses a centrifugal rotor comprising a plurality of peripheral cuvettes spaced radially outward from the collection chamber. A plurality of generally radial inlet channels connects each cuvette to the chamber. Each inlet channel has a discrete flow path for fluid to enter the cuvette and another discrete flow path for gas to exit the cuvette as the cuvette is filled. As the rotor is spun, fluid enters the cuvettes from the collection chamber through the inlet channels, which also allow gas in the cuvettes to escape, thus avoiding the creation of bubbles in the cuvette as the cuvettes are filled.

The apparatus of the present invention includes a centrifugal rotor which may be mounted on a conventional laboratory centrifuge of the type which is commercially available from suppliers, such as Beckman Instruments, Inc., Spinco Division, Fullerton, Calif.; Fisher Scientific, Pittsburgh, Pa.; VWR Scientific, San Francisco, Calif., and the like. Generally, the centrifugal rotors will include a receptacle or other coupling device suitable for mounting on a vertical drive shaft within the centrifuge. The particular design of the receptacle or coupling device will depend on the nature of the centrifuge. The centrifugal rotor of the present invention may be adapted for use with most types of centrifuges which are now available or which may become available so long as the velocity profile can be programmed.

The centrifugal rotor comprises a body structure which maintains a desired geometric pattern or relationship between a plurality of chambers and interconnecting inlet channels, as described in more detail below. Usually, the body will be a substantially solid plate with the chambers and passages formed as spaces or voids in an otherwise solid matrix. Conveniently, such solid plate structures may be formed by laminating a plurality of separately formed layers together into a composite structure such that the chambers and passages are generally formed between adjacent layers.

The individual layers may be formed by injection molding, machining, and combinations thereof. Usually the individual layers will be joined together, typically by a suitable adhesive or ultrasonic welding. The final enclosed volumes are formed when the layers are brought together. Of course, the centrifugal rotor could also be formed as a plurality of discrete components, such as tubes, vessels, chambers, etc., arranged in a suitable structural framework. Such assemblies, however, are generally more difficult to manufacture and are therefore less desirable than those formed in a substantially solid plate.

The centrifugal rotor may be formed from a wide variety of materials and may optionally include two or more materials. Usually, the materials will be transparent, for example clear plastic, so that the presence and distribution of blood, plasma, and other reagents, may be observed within the various internal chambers and passages. Also, the test wells formed within the rotor often require suitable optical paths so that their contents may be observed spectrophotometrically, fluorometrically, or by other visual assessment instruments.

In an exemplary embodiment described below, the rotor is formed of acrylic resin possessing certain optical properties, at least in those areas which define the optical paths. The rotor of the present invention is preferably made of clear plastic, more preferably acrylic. Each cuvette typically contains reagents necessary for a biochemical analysis of its contents. Exposing the fluid to a beam of light may produce an optical effect which is then detected and analyzed. Alternatively, the analysis could involve non-optical features. In such a case the composition of the rotor could be opaque or translucent, although materials are preferably transparent to allow visualization of the sample and reagent.

The apparatus and method of the present invention are suitable for performing a wide variety of analytic procedures beneficially or necessarily performed on plasma. The procedure will generally require combination of plasma with one or more reagent. Preferably, the plasma will undergo a reaction or other change which alters a measurable characteristic of the fluid. For example, a change in color, fluorescence, luminescence, or the like, may be measured by conventional spectrophotometers, fluorometers, light detectors, etc. Alternatively, the change could be detectable by biochemical means.

In some cases, immunoassays and other specific binding assays may be performed in the test wells. Generally, the fluid tested in such assay procedures is homogeneous and does not require a separation step. In other cases, it will be possible to accommodate heterogeneous assay systems by providing a means to separate plasma from the test wells after an immunological reaction step has occurred.

Conventional blood assays which may be performed include glucose, lactate dehydrogenase, serum glutamicoxaloacetic transaminase (SGOT), serum glutamic-pyruvic transaminase (SGPT), blood urea (nitrogen) (BUN), total protein, alkalinity, phosphatase, bilirubin, calcium, chloride, sodium, potassium, magnesium, and the like. This list is not exhaustive and is merely exemplary of the assays which may be performed using the apparatus and method of the present invention.

Usually, these tests will require combination of plasma with at least one reagent which detectably changes the plasma. The change may be detectable by photometrical, biochemical, or other means. The required reagents are well known and amply described in the patent and scientific literature.

Other embodiments of the present invention may utilize regions having different surface textures. For instance, a part of the flow path may be left unpolished, leaving a rough surface texture in that region, while another portion is polished. Alternatively, a portion of the flow path may be rendered hydrophilic whereas another portion is rendered hydrophobic. The treatments to make the surfaces hydrophilic or hydrophobic are well known in the art and need not be recited here. Any appropriate surface treatment may be used.

Referring now to FIG. 1, an analytical rotor 1 constructed in accordance with the principles of the present invention is shown in detail. Rotor 1 is in the form of a substantially solid disk, a plan view of which is shown in FIG. 1. Rotor 1 comprises a holding chamber 3 having a single exit duct 6. An initial volume of fluid, such as whole blood, is introduced into holding chamber 3 by any number of means.

Fluid may be introduced into holding chamber 3 by a variety of means known to the artisan. Manual or automated pipetting or pouring are examples. More preferably, a loading chamber 5 is provided with rotor 1. The sample may be introduced by means of a blood application port (not shown). This port may be formed by injection molding or machining. The sample may travel from the application port to loading chamber 5 by force of gravity, centrifugal force, or a combination of forces.

Once in loading chamber 5, the sample is introduced to holding chamber 3 by entry passage 4. Although only one entry passage 4 is shown, loading chamber 5 could empty into a plurality of entry passages 4. Preferably centrifugal force generated by spinning rotor 1 promotes egress of the sample from loading chamber 5 to entry passage 4, although use of other influences may be practical. Examples include gravity and positive pressure.

The sample emerges from entry passage 4 into holding chamber 3 by use of appropriate force as described above. Exit duct 6 fluidly connects holding chamber 3 to a capillary passage 10. The configurations of exit duct 6 and capillary passage 10 are not critical. The cross section of the duct and the passage may resemble a circle, ellipse, rectangle, or some other geometric form. Preferably, exit duct 6 is a bore in holding chamber 3.

The cross sectional area of capillary passage 10 is such that fluid flow is prevented at a first rotational speed, and permitted at a second higher rotational speed. For whole blood or diluent, the diameter of capillary passage 10 is typically between about 0.05 mm and about 0.25 mm, preferably between about 0.075 mm and about 0.125 mm. The sizes are dependent on the surface tension of the fluid selected and the rotational velocity of the rotor. In addition, the surface tension changes when surfactants are added. The artisan can easily adjust the diameter of the capillary passage to account for these factors.

Capillary passage 10 is in fluid communication with a receiving chamber 8. Receiving chamber 8 is positioned radially outward from holding chamber 3. To deliver fluid from holding chamber 3 to receiving chamber 8, the rotational speed is increased sufficiently to cause centrifugal force to exceed capillary force and thus drain holding chamber 3 into receiving chamber 8. The rotational direction is not critical. It may be clockwise, counterclockwise, or an alteration between these directions.

The rotational speeds to fill holding chamber 3 typically generate a centrifugal force of about 5×g to about 42×g, preferably about 20×g to about 27×g. To deliver fluid to receiving chamber 8 after holding chamber 3 is filled, the rotor's speed is increased sufficiently to cause the centrifugal force to exceed the capillary force and thus drain holding chamber 3 into receiving chamber 8. The higher rotational speeds are typically generate a centrifugal force exceeding about 45×g.

Holding chamber 3 may contain a reagent. The reagent may be any of a number of substances. Examples include, but are not limited to, diluents, aqueous solutions, buffers, organic compounds, dehydrated chemicals, crystals, proteins, and solvents. In a preferred embodiment, the reagent is a marking compound. A nonexclusive list of marking compounds includes dye, fluorescent and phosphorescent substances, radioactive labelling materials, enzymes, biotin, and immunologic compounds. Conveniently, the reagent may coat a solid surface within holding chamber 3. In a most preferred embodiment, the reagent is a marker compound in dry form which is carried by a bead 16 contained within holding chamber 3.

Receiving chamber 8 may be a separation chamber. The components of the separation chamber may include a cell trap formed at its radially-outward periphery and a receptacle region formed along its radially-inward perimeter. The components of a separation chamber are discussed more fully below. As discussed above, collection chamber 24 need not be positioned below the separation chamber. It can, for example, be positioned radially outward of the separation chamber.

Collection chamber 24 is spaced radially inward from a plurality of peripheral cuvettes 28. Each cuvette 28 is connected to collection chamber 24 by an inlet channel 27. Each inlet channel 27 may comprise two discrete flow paths.

This would allow gas to escape easily from cuvette 28 as it is filled, thus preventing the formation of bubbles in cuvette 28. Bubbles can deleteriously affect analyses.

If optical analysis of cuvette 28 contents is contemplated, reflective surfaces (not shown) may be positioned radially inward from each cuvette 28. Said reflective surfaces are capable of deflecting a light beam between a generally horizontal and a generally vertical direction.

Figure 2:
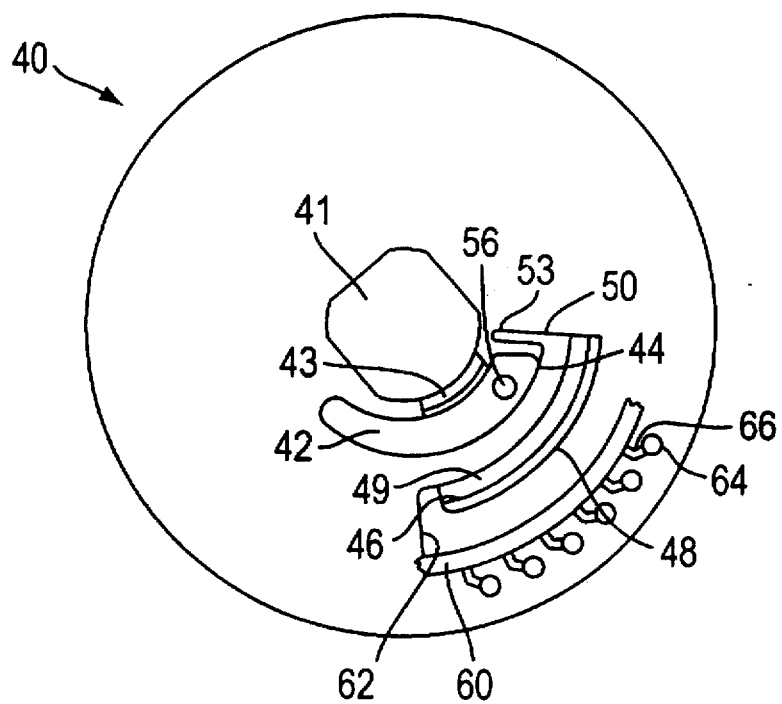
FIG. 2 is a plan view of a rotor in which a siphon is used to control flow between a holding chamber and a receiving chamber, and in which the receiving chamber is a separation chamber including a cell trap.

FIG. 2 shows another embodiment of the present invention, a rotor 40. A fluid is introduced into a loading chamber 41 by any number of means. A holding chamber 42 operates on the same principles as holding chamber 3 described in FIG. 1. A passage 43 connects loading chamber 41 to holding chamber 42. A siphon 50 connects an exit duct 44 to a separation chamber 46. An elbow 53 of siphon 50 is positioned so that it is substantially the same distance from center 30 of rotor 40 as the radially most inward point of holding chamber 42. A reagent may be placed in holding chamber 42 conveniently by means of a bead 56.

As rotor 40 initially spins, a fluid in holding chamber 42 does not move past elbow 53 of siphon 50. Rotor 40 is then stopped, or slowed sufficiently, and capillary action pulls the fluid just beyond elbow 53 and siphon 50 is "primed." When rotation of rotor 40 resumes or is increased, centrifugal and capillary forces pull the fluid out of holding chamber 42 into separation chamber 46. Separation chamber 46 is disposed radially outward from holding chamber 42.

The components of separation chamber 46 include a cell trap 48 formed at its radially-outward periphery and a receptacle region 49 formed along its radially-inward perimeter. A capillary region is formed between receptacle region 49 and cell trap 48 in order to inhibit the backflow of cells after they have entered cell trap 48 as a result of centrifugal separation.

Receptacle region 49 provides a volume which is capable of receiving whole blood or other biological fluid (optionally combined with a diluent or reagent) and which retains plasma or other separated fluid after centrifugation. An axial port (not shown) is conveniently formed as an annular passage which penetrates the entire thickness of rotor 40. Thus separated plasma may flow downward from receptacle region 49 of chamber 46 through a passage 62 into a collection chamber 60 formed in bottom layer (not shown), as described above. As discussed above, collection chamber 60 need not be positioned below separation chamber 46. It can, in a preferred embodiment, be positioned radially outward from separation chamber 46.

Briefly, as rotor 40 spins, a fluid is delivered to separation chamber 46. To deliver the fluid, the speed of rotor 40 is increased sufficiently to siphon fluid 58 from holding chamber 42 into separation chamber 46. The rotational speeds to empty holding chamber 42 are preferably the same as those to empty holding chamber 3. After entering collection chamber 60, the fluid moves through passage 66 to cuvettes 64 as discussed above.

The above description of the embodiments of the invention and the attached drawings are provided by way of illustration only. Numerous other embodiments will be apparent to one of ordinary skill in the art. Thus, limitations on the scope of the subject invention are to be found only in the claims set forth below.

What is claimed is:

1. A method for delivering, in a centrifugal rotor, a fluid from a holding chamber to a receiving chamber positioned radially outward from the holding chamber, the holding chamber having an exit duct connected through a capillary passage to said receiving chamber, the method comprising the steps of:

spinning the rotor at a first rotational speed, thereby transferring said fluid from a loading chamber positioned radially inward from said holding chamber through an entry channel into said holding chamber; and spinning the rotor at a second higher rotational speed, thereby transferring the fluid from the holding chamber to the receiving chamber through said exit duct and capillary passage, wherein said capillary passage has a cross sectional area less than the cross sectional area of the entry channel such that flow of fluid from the holding chamber to the receiving chamber is prevented at the first rotational speed and allowed at said second higher rotational speed.

2. The method of claim 1, wherein the holding chamber is a mixing chamber.

3. The method of claim 2, wherein the mixing chamber comprises a marker compound.

4. A method for contacting, in a centrifugal rotor, a fluid with a reagent, the method comprising the steps of:

spinning the rotor at a first rotational speed, thereby introducing said fluid from a loading chamber in said rotor through an entry channel into a holding chamber positioned in said rotor radially outward from said loading chamber, said holding chamber having an exit duct and comprising a reagent coated on a solid surface therein where said fluid combines with said reagent thereby forming a mixture and spinning the rotor at a second higher rotational speed, thereby transferring the fluid from the holding chamber to a receiving chamber positioned radially outward from the holding chamber through the exit duct and a capillary passage wherein said capillary passage has a cross sectional area such that flow of fluid from the holding chamber to the receiving chamber is prevented at the first rotational speed and allowed at said second higher rotational speed.

5. The method of claim 4 further comprising the step of changing the direction of rotation after the fluid is introduced into the holding chamber thereby mixing the fluid and the reagent.

6. The method of claim 4, wherein the fluid is a biological fluid.

7. The method of claim 4, wherein the fluid is a diluent.

8. The method of claim 4, wherein said solid surface is a bead disposed within said holding chamber.

9. A method of delivering, in a centrifugal rotor, a fluid to a separation chamber having a cell trap, the method comprising:

spinning the rotor to effect a radial outward flow of the fluid from a loading chamber through a passage into a holding chamber having an exit duct;

stopping the rotation of the rotor, thereby priming a siphon connecting the exit duct to the separation chamber; and spinning the rotor, thereby delivering the fluid to the separation chamber through the exit duct and the siphon.

10. A method of delivering, in a centrifugal rotor, a fluid to a metering chamber, the method comprising:

spinning the rotor to effect a radial outward flow of the fluid from a loading chamber through a passage into a holding chamber having an exit duct;

stopping the rotation of the rotor, thereby priming a siphon connecting the exit duct to the metering chamber; and spinning the rotor, thereby delivering the fluid to the metering chamber through the exit duct and the siphon.

* * * * *